US008912011B2

(12) United States Patent
Tully et al.

(10) Patent No.: US 8,912,011 B2
(45) Date of Patent: Dec. 16, 2014

(54) ANTIBODIES TO SULFATED CARBOHYDRATES

(75) Inventors: Sarah E. Tully, Washington, DC (US); Linda C. Hsieh-Wilson, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 797 days.

(21) Appl. No.: 12/511,941

(22) Filed: Jul. 29, 2009

(65) Prior Publication Data

US 2010/0071080 A1     Mar. 18, 2010

Related U.S. Application Data

(63) Continuation of application No. 11/751,863, filed on May 22, 2007, now Pat. No. 7,745,584.

(60) Provisional application No. 60/802,413, filed on May 22, 2006.

(51) Int. Cl.
*G01N 33/53* (2006.01)
*C07K 16/18* (2006.01)
*A61K 39/00* (2006.01)

(52) U.S. Cl.
CPC ........... *C07K 16/18* (2013.01); *A61K 2039/505* (2013.01)
USPC ....................................................... 436/547

(58) Field of Classification Search
USPC ....................................... 436/547; 530/387.1
See application file for complete search history.

(56) References Cited

U.S. PATENT DOCUMENTS

| | | | |
|---|---|---|---|
| 4,376,110 A | 3/1983 | David et al. | |
| 4,399,216 A | 8/1983 | Axel et al. | |
| 4,740,461 A | 4/1988 | Kaufman | |
| 4,883,751 A * | 11/1989 | Gitel et al. | 435/7.92 |
| 4,912,040 A | 3/1990 | Kaufman et al. | |
| 4,946,778 A | 8/1990 | Ladner et al. | |
| 4,959,455 A | 9/1990 | Clark et al. | |
| 5,185,245 A * | 2/1993 | Heimer | 435/7.1 |
| 5,821,337 A * | 10/1998 | Carter et al. | 530/387.3 |
| 6,200,564 B1 | 3/2001 | Lamont et al. | |
| 2003/0073147 A1* | 4/2003 | Alderete et al. | 435/7.31 |
| 2006/0025379 A1* | 2/2006 | Hsieh-Wilson et al. | 514/54 |
| 2008/0009607 A1 | 1/2008 | Tully et al. | |
| 2008/0124339 A1 | 5/2008 | Pullen et al. | |

FOREIGN PATENT DOCUMENTS

| | | | |
|---|---|---|---|
| WO | WO 92/22653 A1 | 12/1992 | |
| WO | WO 93/21319 A1 | 10/1993 | |
| WO | WO 2004017910 A2 * | 3/2004 | |

OTHER PUBLICATIONS

Stevens et al (JBC, 258:5977-5984, 1993).*
Habuchi et al (An. Bio., 310:129-136, 2002).*
Campbell (Monoclonal Antibody Technology, Laboratory Techniques in Biochemistry and Molecular Biology, Elsevier Science Publishers B.V.: Amsterdam, The Netherlands, vol. 13, pp. 1-32, 1984).*
Bergefell, et al. Chondroitin sulfate characterized by the E-disaccharide unit is a potent inhibitor of herpes simplex virus infectivity and provides the virus binding sites on gro2C cells. J Biol Chem. Sep. 16, 2005;280(37):32193-9.
Bradbury, et al. Chondroitinase ABC promotes functional recovery after spinal cord injury. Nature. Apr. 11, 2002;416(6881):636-40.
Caldas, et al. Humanization of the anti-CD18 antibody 6.7: an unexpected effect of a framework residue in binding to antigen. Mol Immunol. May 2003;39(15):941-52.
Chien, et al. Significant structural and functional change of an antigen-binding site by a distant amino acid substitution: proposal of a structural mechanism. Proc Natl Acad Sci U S A. Jul. 1989;86(14):5532-6.
Cote, et al. Generation of human monoclonal antibodies reactive with cellular antigens. Proc Natl Acad Sci U S A. Apr. 1983;80(7):2026-30.
Cote, et al. The EBV-Hybridoma technique and its application to human lung cancer. In Monoclonal antibodies and cancer therapy. Alan R. Liss, Inc. 1985; 77-96.
Fournier, et al. Identification of a receptor mediating Nogo-66 inhibition of axonal regeneration. Nature. Jan. 18, 2001;409(6818):341-6.
Fundamental Immunology p. 242 (William E. Paul, M.D. ed., 3d ed; 1993.).
Gama, et al. Sulfation patterns of glycosaminoglycans encode molecular recognition and activity. Nat Chem Biol. Sep. 2006;2(9):467-73.
Garland, Ed. Immunobiology. Janeway, 2001, pp. 102-103.
Giusti, et al. Somatic diversification of S107 from an antiphosphocholine to an anti-DNA autoantibody is due to a single base change in its heavy chain variable region. Proc Natl Acad Sci U S A. May 1987;84(9):2926-30.
Green, et al. Antigen-specific human monoclonal antibodies from mice engineered with human Ig heavy and light chain YACs. Nat Genet. May 1994;7(1):13-21.
Gussow, et al. Humanization of monoclonal antibodies. Methods Enzymol 1991;203:99-121.
Habeeb, A. F. Determination of free amino groups in proteins by trinitrobenzenesulfonic acid. Anal Biochem. Mar. 1966;14(3):328-36.
Holm, et al. Functional mapping and single chain construction of the anti-cytokeratin 8 monoclonal antibody TS1. Mol Immunol. Feb. 2007;44(6):1075-84.
Holt, et al. Sugar codes for axons? Neuron. Apr. 21, 2005;46(2):169-72.
Huse, et al. Generation of a large combinatorial library of the immunoglobulin repertoire in phage lambda. Science. Dec. 8, 1989;246(4935):1275-81.

(Continued)

*Primary Examiner* — Brad Duffy

(74) *Attorney, Agent, or Firm* — Wilson Sonsini Goodrich & Rosati

(57) ABSTRACT

The present invention relates to antibodies and antigen-binding portions thereof that specifically bind to chondroitin sulfate, particularly CS-A, CS-C and CS-E tetrasaccharides. The present invention also relates to methods of making anti-CS antibodies, pharmaceutical compositions comprising these antibodies and methods of using the antibodies and compositions thereof for diagnosis and treatment.

4 Claims, 5 Drawing Sheets

(56) References Cited

OTHER PUBLICATIONS

Immunobiology for life scientists (Wiley, Ed. Eales, p. 14, 2003.
Ito, et al. Structural characterization of the epitopes of the monoclonal antibodies 473HD, CS-56, and MO-225 specific for chondroitin sulfate D-type using the oligosaccharide library. Glycobiology. Jun. 2005;15(6):593-603.
Jacquinet, et al. Multigram syntheses of the disaccharide repeating units of chondroitin 4- and 6-sulfates. Carbohydr-Res. Dec. 31, 1998; 314(3-4): 283-8.
Kitagawa, et al. Developmental regulation of the sulfation profile of chondroitin sulfate chains in the chicken embryo brain. J Biol Chem. Dec. 12, 1997;272(50):31377-81.
Kohler, et al. Continuous cultures of fused cells secreting antibody of predefined specificity. Nature. Aug. 7, 1975;256(5517):495-7.
Kozbor, et al. The production of monoclonal antibodies from human lymphocytes. Immunology Today. 1983; 4:72-79.
MacCallum, et al. Antibody-antigen interactions: contact analysis and binding site topography. J Mol Biol. Oct. 11, 1996;262(5):732-45.
Mariuzza, et al. The structural basis of antigen-antibody recognition. Annu Rev Biophys Biophys Chem. 1987;16:139-59.
Marsh, et al. Signal transduction events mediated by the BDNF receptor gp 145trkB in primary hippocampal pyramidal cell culture. J Neurosci. Oct. 1993;13(10):4281-92.
Moon, et al. Regeneration of CNS axons back to their target following treatment of adult rat brain with chondroitinase ABC. Nat Neurosci. May 2001;4(5):465-6.
Nandini, et al. Structural and functional characterization of oversulfated chondroitin sulfate/dermatan sulfate hybrid chains from the notochord of hagfish. Neuritogenic and binding activities for growth factors and neurotrophic factors. J Biol Chem. Dec. 3, 2004;279(49):50799-809.
Plaas, et al. Glycosaminoglycan sulfation in human osteoarthritis. Disease-related alterations at the non-reducing termini of chondroitin and dermatan sulfate. J Biol Chem. May 15, 1998;273(20):12642-9.
Rudikoff, et al. Single amino acid substitution altering antigen-binding specificity. Proc Natl Acad Sci U S A. Mar. 1982;79(6):1979-83.
Shi, et al. Luteolin sensitizes tumor necrosis factor-alpha-induced apoptosis in human tumor cells. Oncogene. Oct. 7, 2004;23(46):7712-21.
Shipp, et al. Profiling the sulfation specificities of glycosaminoglycan interactions with growth factors and chemotactic proteins using microarrays. Chem Biol. Feb. 2007; 14(2):195-208.
Shirayev, et al. Synthesis of Novel Adamantylalkoxyurea Derivatives from 2-(1-Adamantylimino)-1,3-oxathiolane. Journal of Synthetic Organic Chemistry. 1997; 1:38-40.
Smetsers, et al. Human Single-Chain Antibodies Reactive with Native Chondroitin Sulfate Detect Chondroitin Sulfate Alterations in Melanoma and Psoriasis. J Invest Dermatol. Mar. 2004;122(3):707-16.
Sotogaku, et al. Activation of phospholipase C pathways by a synthetic chondroitin sulfate-E tetrasaccharide promotes neurite outgrowth of dopaminergic neurons. J Neurochem. Oct. 2007;103(2):749-60.
Suzuki, et al. Formation of three types of disulfated disaccharides from chondroitin sulfates by chondroitinase digestion. J Biol Chem. Apr. 10, 1968;243(7):1543-50.
Tamura, et al. Synthetic approach towards sulfated chondroitin di-, tri- and tetrasaccharides corresponding to the repeating unit. Carbohydr Res. Dec. 1997;305(1):43-63.
Taylor, et al. A colorimetric method for the quantitation of uronic acids and a specific assay for galacturonic acid. Anal Biochem. Feb. 14, 1992;201(1):190-6.
Tully, et al. A chondroitin sulfate small molecule that stimulates neuronal growth. J. Am. Chem. Soc. 2004; 126:7736-7737.
Tully, et al. Discovery of a TNF-alpha antagonist using chondroitin sulfate microarrays. J Am Chem Soc. Jun. 21, 2006;128(24):7740-1.
Volpi, N. Disaccharide mapping of chondroitin sulfate of different origins by high-performance capillary electrophoresis and high-performance liquid chromatography. Carbohyd. Polym. 2004; 55, 273-281.
Winkler, et al. Changing the antigen binding specificity by single point mutations of an anti-p24 (HIV-1) antibody. J Immunol. Oct. 15, 2000;165(8):4505-14.
Yamagata, et al. A monoclonal antibody that specifically recognizes a glucuronic acid 2-sulfate-containing determinant in intact chondroitin sulfate chain. J Biol Chem. Mar. 25, 1987;262(9):4146-52.
Yamagata, et al. Tissue variation of two large chondroitin sulfate proteoglycans (PG-M/versican and PG-H/aggrecan) in chick embryos. Anat Embryol (Berl). May 1993;187(5):433-44.
Yeung, et al. An essential role for the interferon-inducible, double-stranded RNA-activated protein kinase PKR in the tumor necrosis factor-induced apoptosis in U937 cells. Proc Natl Acad Sci U S A. Oct. 29, 1996;93(22):12451-5.
Habuchi, et al. Enzymatic synthesis of chondroitin sulfate E by N-acetylgalactosamine 4-sulfate 6-O-sulfotransferase purified from squid cartilage. An Bio. 2002; 310(2):129-136.
Stevens, et al. Synthesis of chondroitin sulfate E glycosaminoglycan onto p-nitrophenyl-β-d-xyloside and its localization to the secretory granules of rat serosal mast cells and mouse bone marrow-derived mast cells. JBC.1983; 258;5977-5984.

* cited by examiner

US 8,912,011 B2

ANTIBODIES TO SULFATED CARBOHYDRATES

CROSS-REFERENCE TO RELATED APPLICATIONS

This application claims the benefit of and is a Continuation Application of U.S. application Ser. No. 11/751,863, filed May 22, 2007, now U.S. Pat. No. 7,745,584, which claims the benefit of and priority to U.S. Provisional Application No. 60/802,413, filed May 22, 2006, each of which is incorporated herein by reference in its entirety.

STATEMENT REGARDING FEDERALLY SPONSORED R&D

The U.S. Government has certain rights in this invention pursuant to Grant No. NS045061 awarded by the National Institutes of Health.

BACKGROUND OF THE INVENTION

1. Field of the Invention

The invention relates generally to antibodies to sulfated carbohydrates, particularly chondroitin sulfate A (CS-A), chondroitin sulfate C(CS-C) and chondroitin sulfate E (CS-E). Antibodies to CS-A, CS-C and CS-E are provided, as are methods of using such antibodies.

2. Description of the Related Art

Glycosaminoglycans have an inherent capacity to encode functional information that rivals DNA, RNA and proteins. Specifically, these polysaccharides display diverse patterns of sulfation that are tightly regulated in vivo. Kitagawa, H. et al., *J. Biol. Chem.* 272, 31377-31381 (1997). Plaas, A. H. K. et al., *J. Biol. Chem.* 273, 12642-12649 (1998). Chondroitin sulfate (CS) glycosaminoglycans play important roles in biological processes such as neural development, viral invasion, cancer metastasis and spinal cord injury. The three major sulfation motifs found in vivo, CS-A, CS-C and CS-E, differ only subtly in their sulfation pattern and are identical in terms of stereochemistry and sugar composition. Although glycosaminoglycans contribute to diverse physiological processes, an understanding of their molecular mechanisms has been hampered by the inability to access homogeneous glycosaminoglycan structures.

SUMMARY OF THE INVENTION

Isolated antibodies to chondroitin sulfate are disclosed in accordance with some embodiments of the present invention. In some embodiments, the antibodies are able to bind specifically to a single type of chondroitin sulfate oligosaccharide, wherein the chondroitin sulfate oligosaccharide is selected from the group consisting of a chondroitin sulfate A (CS-A) oligosaccharide, a chondroitin sulfate C(CS-C) oligosaccharide, and a chondroitin sulfate E (CS-E) oligosaccharide. The oligosaccharide may be, for example, a tetrasaccharide or a disaccharide.

In some embodiments, an isolated antibody to chondroitin sulfate is an isolated humanized antibody.

Antibodies to chondroitin sulfate can be used to modulate the activity of chondroitin sulfate binding proteins. For example, methods of modulating TNF-α activity and midkine activity using an antibody that binds to chondroitin sulfate E is disclosed in accordance with other embodiments. An antibody to chondroitin sulfate E can also be used to modulate neuronal growth. In addition, methods of modulating brain derived neurotrophic factor (BDNF) activity using an antibody that binds to a chondroitin sulfate selected from CS-E, CS-A, and CS-C are provided.

DETAILED DESCRIPTION OF THE PREFERRED EMBODIMENT

Figure 1A:
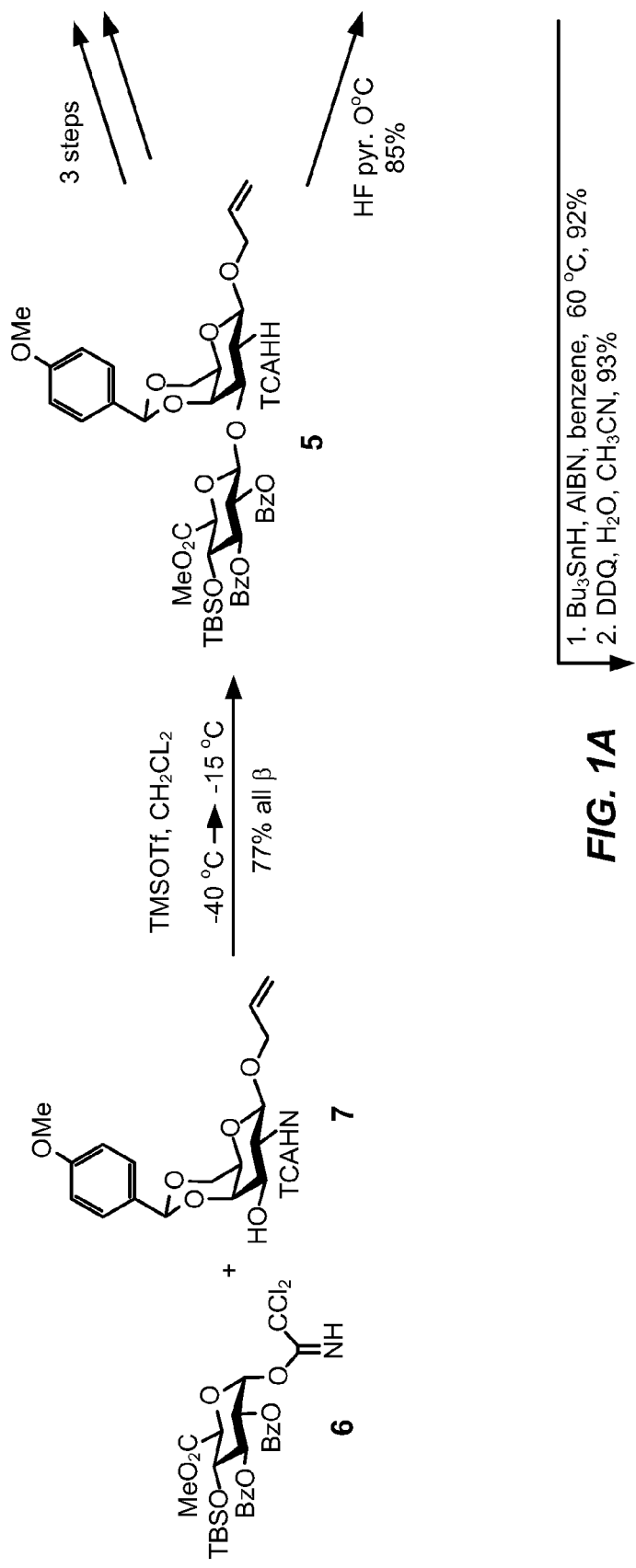
FIGS. 1 A-D depict the synthesis of CS tetrasaccharides of defined sulfation pattern, stereochemistry and chain length. Tetrasaccharides were assembled from a core disaccharide building block 5 and elaborated to install distinct sulfation motifs. This modular, convergent approach permits access to a variety of sulfation patterns, including three important sulfation motifs found in the mammalian brain CS-E, CS-C and CS-A) and the CS-R motif, which has the same overall electrostatic charge as CS-E and can be used to evaluate further the importance of sulfate group orientation. The following abbreviations are used in FIGS. 1 A-D: TMSOTf, trimethylsilyl trifluoromethansulfonate; $CH_2Cl_2$, dichloromethane; HF.pyr, hydrogen fluoride-pyridine complex; $Bu_3SnH$, tri-n-butyltin hydride; AIBN, 2,2'-azobisisobutyronitrile; DDQ, 2,3-dichloro-5,6-dicyano-1,4-benzoquinone; $H_2O$, water; $CH_3CN$, acetonitrile; $SO_3$.TMA, sulfur trioxide-trimethylamine complex; DMF, dimethylformamide; LiOH, lithium hydroxide; $H_2O_2$, hydrogen peroxide; NaOH, sodium hydroxide; MeOH, methanol; BzCN, benzoyl cyanide; pyr, pyridine; $PhCH(OMe)_2$, benzaldehyde dimethyl acetal; CSA, DL-10-camphorsulfonic acid; $SO_3$.TEA, sulfur trioxide-triethylamine complex; AcOH, acetic acid; TBS, t-butyldimethylsilyl; Bz, benzoyl; TCA, trichloroacetyl; Me, methyl; Ac, acetyl.
Figure 1B:
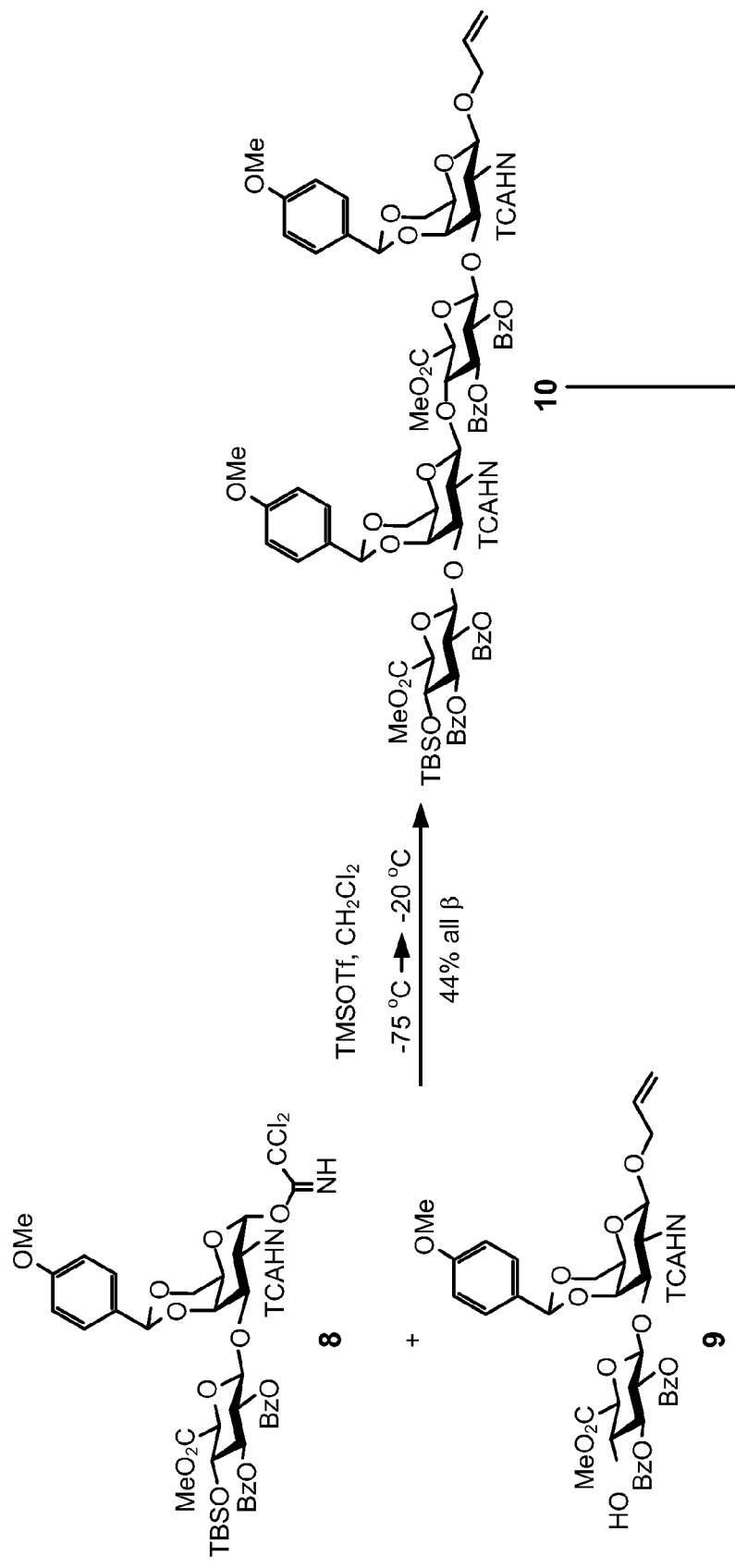
Figure 1C:
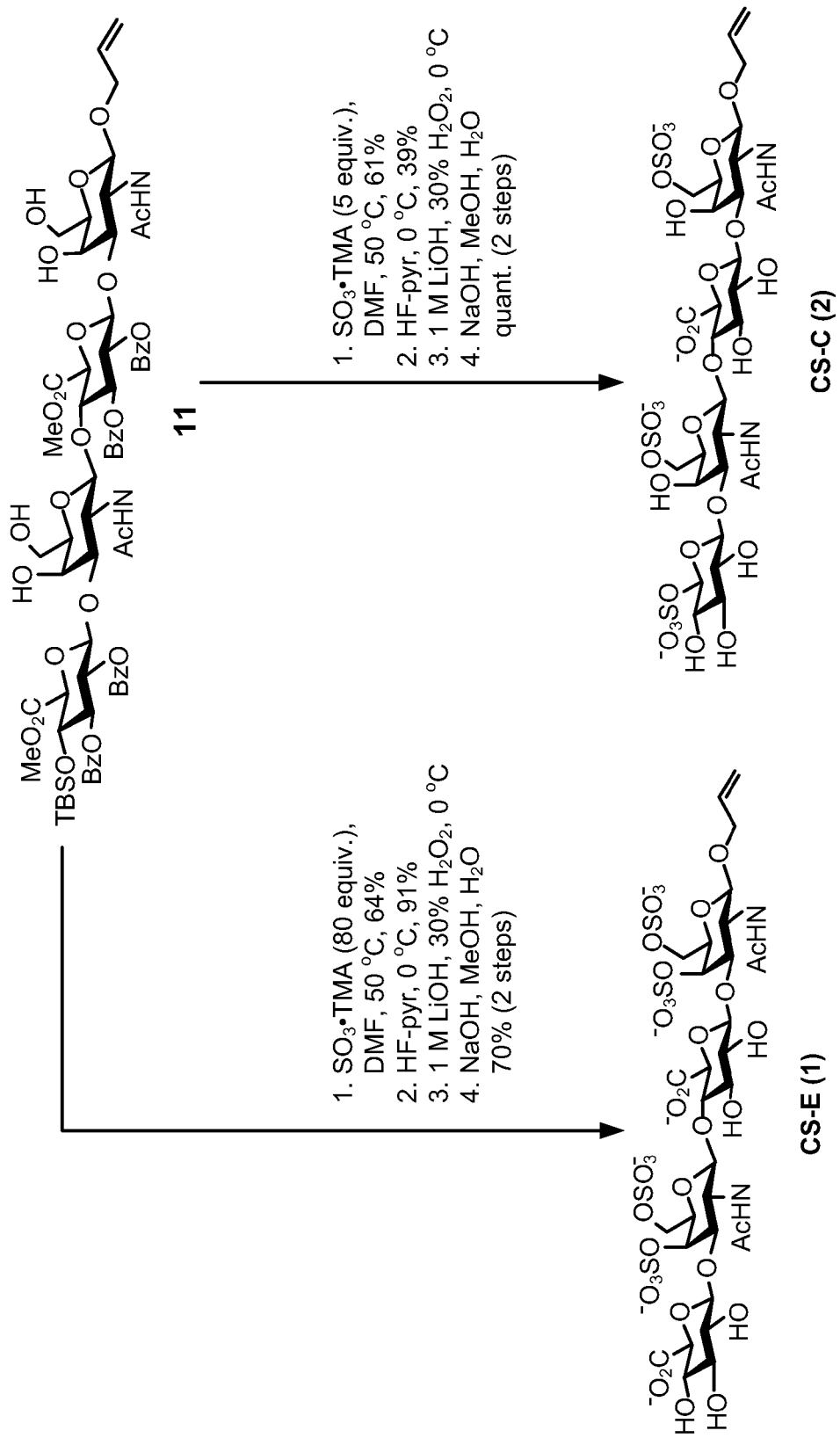
Figure 1D:
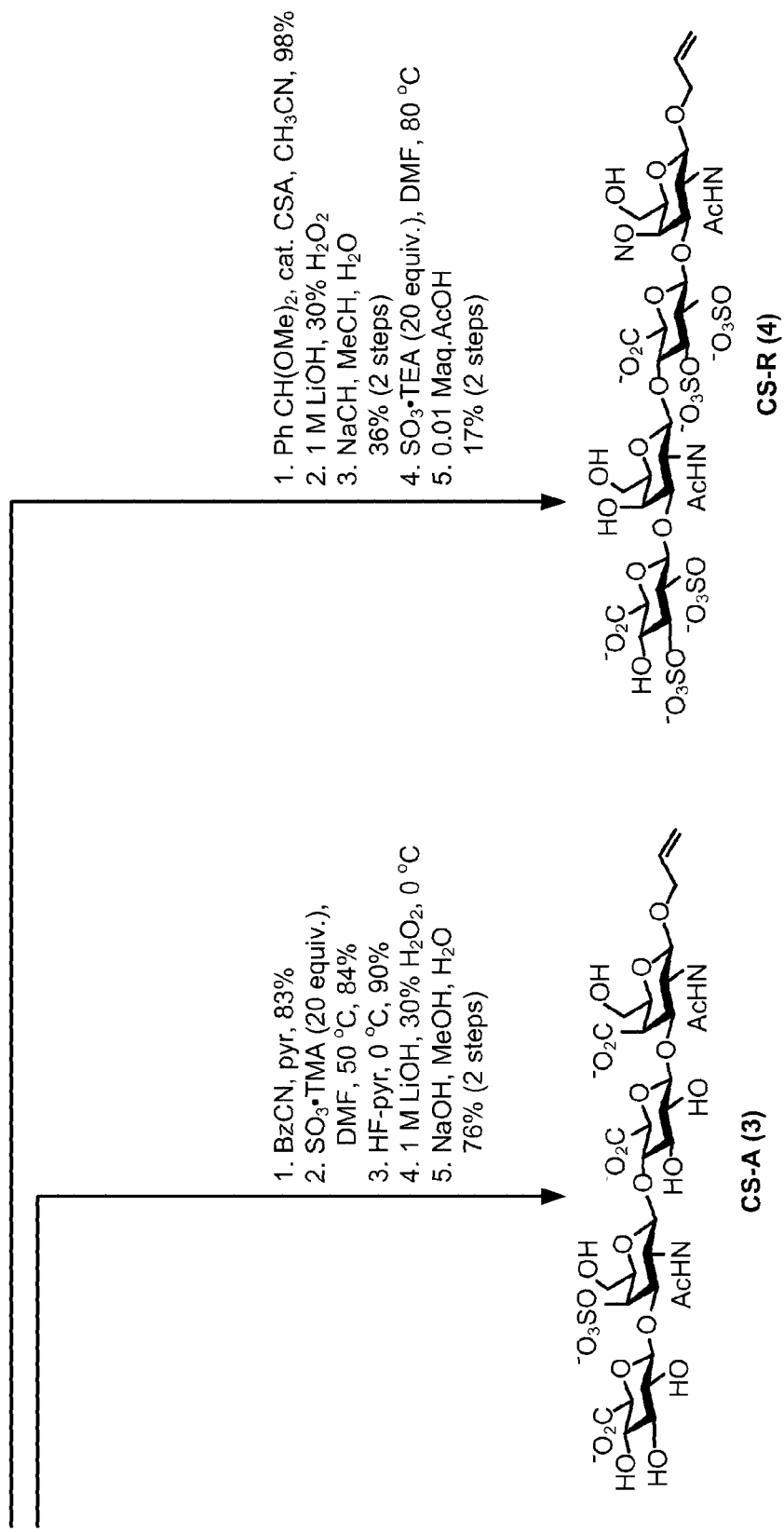

Although several strategies have been developed, no methods to systematically explore the role of specific sulfation sequences existed prior to the developments described herein. For instance, genetic approaches that target a sulfotransferase gene perturb multiple sulfation patterns throughout the polysaccharide chain and cannot be used to study the impact of a single structural motif. Holt, C. E. et al., *Neuron* 46, 169-172 (2005). Biochemical methods afford a mixture of heterogeneously sulfated compounds of poorly defined linear sequence (Nandini, C. D. et al., *J. Biol. Chem.* 279, 50799-50809 (2004)), thereby complicating efforts to relate a biological function to a specific sulfation sequence.

Methods for the assembly of well-defined chondroitin sulfate oligosaccharides using a convergent, synthetic approach are disclosed in accordance with some embodiments of the present invention. In some embodiments, methods are provided using chemical synthesis to generate oligosaccharides representing each of the three major subclasses of CS found in vivo: CS-A, CS-C, and CS-E.

The ability to synthesize CS led to the ability to make antibodies that specifically recognize a single CS subclass. Thus, antibodies to chondroitin sulfate and methods for using antibodies to chondroitin sulfate are disclosed in accordance with some embodiments. Isolated antibodies are disclosed that bind to a chondroitin sulfate, particularly one of CS-A, CS-C and CS-E. In some embodiments the antibodies can be humanized or fully human monoclonal antibodies that bind to chondroitin sulfate with high affinity, high potency, or both. In some embodiments, the antibodies specifically bind to regions of the CS that prevent the CS from interacting with a chondroitin sulfate binding protein and thus can be used to modulate the activity of CS binding proteins.

Antibodies that specifically recognize one or more epitopes on a single subtype chondroitin sulfate are disclosed in accordance with some embodiments. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies disclosed herein may be used, for example, in the detection of chondroitin sulfate in a biological sample. In some embodiments, the anti-chondroitin sulfate antibodies (anti-CS antibodies) can be utilized as part of a technique whereby samples are analyzed for changes in one or more particular types of chondroitin sulfate expression. In some embodiments, the anti-CS antibodies can be utilized as part of a diagnostic or prognostic technique whereby patients may be tested for abnormal amounts or changes in the amounts of one or more chondroitin sulfates.

Antibodies that recognize specific CS subtypes may also be utilized in conjunction with, for example, compound screening schemes, as described below for the evaluation of the effect of test compounds on expression and/or activity of chondroitin sulfate. Such antibodies may additionally be used as a method for the inhibition of normal or abnormal chondroitin sulfate activity and for the inhibition of binding of chondroitin sulfate binding proteins to other proteins. Thus, such antibodies may, therefore, be utilized, for example, as part of treatment methods.

In some embodiments, methods of using antibodies to chondroitin sulfate to modulate a CS binding molecule activity such as, for example, growth factor activity, are provided. For example an antibody to CS-E could be used to treat inflammation mediated by the CS binding protein TNFα. Other anti-CS antibodies could be used to modulate cell growth, such as neuronal growth.

In addition, embodiments of the invention include methods of using these anti-CS antibodies as a treatment for a disease. For example, the antibodies are useful for treating neurological disorders, including, for example, Alzheimer's disease, arthritis, spinal cord injury or Parkinson's disease. Embodiments of the invention include articles of manufacture comprising the antibodies. For example, one embodiment of the invention is an assay kit comprising chondroitin sulfate antibodies that is used to screen for diseases or disorders associated with chondroitin sulfate activity. In some embodiments, the kit includes a biomarker, allowing one to determine the effectiveness of the antibody in a particular patient.

Embodiments of the invention also include cells for producing the disclosed antibodies.

DEFINITIONS

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Generally, nomenclatures utilized in connection with, and techniques of, cell and tissue culture, molecular biology, and protein and oligo- or polynucleotide chemistry and hybridization described herein are those well known and commonly used in the art, as described in various general and more specific references such as those that are cited and discussed throughout the present specification. See e.g. Singleton et al., *Dictionary of Microbiology and Molecular Biology* 2$^{nd}$ ed., J. Wiley & Sons (New York, N.Y. 1994); Sambrook et al. Molecular Cloning: A Laboratory Manual (2d ed., Cold Spring Harbor Laboratory Press, Cold Spring Harbor, N.Y. (1989)), which is incorporated herein by reference. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. Standard techniques are also used for chemical syntheses, chemical analyses, pharmaceutical preparation, formulation, and delivery, and treatment of patients except as may be discussed herein.

As utilized in accordance with the present disclosure, the following terms, unless otherwise indicated, shall be understood to have the following meanings:

"Monosaccharide," as used herein, refers to a polyhydroxy alcohol containing either an aldehyde or a ketone group, i.e., a simple sugar. Monosaccharide includes reference to naturally occurring simple sugars as well as simple sugars which have been chemically modified. Modified monosaccharides include, but are not limited to, monosaccharides that have increased or decreased sulfation or that have modified carboxyl, amino or hydroxyl groups.

"Polysaccharide" as used herein, refers to a linear or branched polymer of two or more monosaccharides that are linked by means of glycosidic linkages.

"Polyanion," as used herein, refers to a molecule that possesses a large number of negative charges. "Polyanionic carbohydrates," as used herein, includes reference to carbohydrates that possess a large number of negative charges.

"Glycosaminoglycan," as used herein, includes reference to a polysaccharide composed of repeating disaccharide units. The disaccharides contain an amino sugar (i.e., glucosamine or galactosamine) and one other monosaccharide, which may be, for example, a uronic acid (i.e., glucuronic acid or iduronic acid) as in hyaluronic acid, heparin, heparan sulfate, chondroitin sulfate or dermatan sulfate, or galactose as in keratan sulfate. The glycosaminoglycan chain may be sulfated on either moiety of the repeating disaccharide.

As used herein, "chondroitin" refers generally to chondroitin, salts thereof such as chondroitin sulfate, esters thereof, and mixtures thereof. "Chondroitin sulfate" (CS), as used herein, refers generally to at least one unit in a chondroitin sulfate chain. A chondroitin sulfate chain is a sulfated glycosaminoglycan (GAG) composed of a chain of alternating sugars (N-acetylgalactosamine and glucuronic acid).

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Chothia et al. *J. Mol. Biol.* 186:651 (1985); Novotny and Haber, *Proc. Natl. Acad. Sci. U.S.A.* 82:4592 (1985); Chothia et al., *Nature* 342: 877-883 (1989)).

The term "antibody" herein is used in the broadest sense and specifically covers intact monoclonal antibodies, polyclonal antibodies, multispecific antibodies (e.g. bispecific antibodies) formed from at least two intact antibodies, and antibody fragments including Fab and F(ab)'2, so long as they exhibit the desired biological activity. The "light chains" of antibodies (immunoglobulins) from any vertebrate species can be assigned to one of two clearly distinct types, called κ and λ, based on the amino acid sequences of their constant domains. Binding fragments can be produced by recombinant DNA techniques, or by enzymatic or chemical cleavage of intact antibodies. Binding fragments include Fab, Fab', F(ab')$_2$, Fv, and single-chain antibodies, as described in more detail below. An antibody other than a "bispecific" or "bifunctional" antibody is understood to have each of its binding sites identical.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the Ig light-chain and heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of the β-sheet structure. The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector functions, such as participation of the antibody in antibody-dependent cellular toxicity.

In some embodiments, the antibodies provided herein are neutralizing in that they inhibit binding of chondroitin sulfate to a chondroitin sulfate binding protein, such as, for example, TNF-α. In some embodiments they inhibit binding by at least about 20%, 40%, 60% or 80%, and more usually greater than about 85% (as measured in an in vitro competitive binding assay).

Depending on the amino acid sequence of the constant domain of their heavy chains, intact antibodies can be assigned to different "classes." There are five major classes of intact antibodies: IgA, IgD, IgE, IgG, and IgM, and several of these can be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ respectively. The subunit structures and three-dimensional configurations of different classes of immunoglobulins are well known.

The term "monoclonal antibody" as used herein refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they can be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention can be made by the hybridoma method first described by Kohler et al., *Nature*, 256:495 (1975), or can be made by recombinant DNA methods (see, e.g., U.S. Pat. No. 4,816,567).

An "isolated" antibody is one which has been identified and separated and/or recovered from a component of its natural environment. Contaminant components of its natural environment are materials which would interfere with diagnostic or therapeutic uses for the antibody, and can include enzymes, hormones, and other proteinaceous or nonproteinaceous solutes. In preferred embodiments, the antibody will be purified (1) to greater than 95% by weight of antibody as determined by the Lowry method, and terminal or internal amino acid sequence by use of a spinning cup sequenator, or (2) to homogeneity by SDS-PAGE under reducing or nonreducing conditions using, for example, Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

A "neutralizing antibody" is an antibody molecule that is able to eliminate or significantly reduce an effector function of a target antigen to which it binds. Accordingly, a "neutralizing" chondroitin sulfate antibody is capable of eliminating or significantly reducing an effector function, such as, for example, binding of a chondroitin sulfate binding protein to another protein, where the binding is mediated by chondroitin sulfate. In one embodiment, a neutralizing antibody will reduce an effector function by 1-10, 10-20, 20-30, 30-50, 50-70, 70-80, 80-90, 90-95, 95-99, 99-100%.

Digestion of antibodies with the enzyme papain results in two identical antigen-binding fragments, known also as "Fab" fragments, and a "Fc" fragment, having no antigen-binding activity but having the ability to crystallize. Digestion of antibodies with the enzyme pepsin results in the a F(ab')$_2$ fragment in which the two arms of the antibody molecule remain linked and comprise two-antigen binding sites. The F(ab')$_2$ fragment has the ability to crosslink antigen.

"Fab" when used herein refers to a fragment of an antibody that comprises the constant domain of the light chain and the CH1 domain of the heavy chain.

"Fv" is the minimum antibody fragment that contains a complete antigen-recognition and binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-62 (L2), and 89-97 (L3) in the light chain variable domain and 31-55 (H1), 50-65 (H2) and 95-102 (H3) in the heavy chain variable domain; Kabat et al., *Sequences of Proteins of Immunological Interest*, 5$^{th}$ Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 ((H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

The term "complementarity determining regions" or "CDRs" when used herein refers to parts of immunological receptors that make contact with a specific ligand and determine its specificity. The CDRs of immunological receptors are the most variable part of the receptor protein, giving receptors their diversity, and are carried on six loops at the distal end of the receptor's variable domains, three loops coming from each of the two variable domains of the receptor.

The term "epitope" is used to refer to binding sites for antibodies on antigens. Epitopic determinants usually consist of chemically active surface groupings of molecules such as amino acids or sugar side chains and usually have specific three dimensional structural characteristics, as well as specific charge characteristics.

An antibody is said to bind an antigen when the dissociation constant ("$K_D$") is ≤10 μM, preferably ≤1 μM, more preferably ≤100 nM and most preferably ≤10 nM. An increased or greater dissociation constant means that there is less affinity between the epitope and the antibody. In other words, that the antibody and the epitope are less favorable to bind or stay bound together. A decreased or lower equilibrium constant means that there is a higher affinity between the epitope and the antibody. In other words, it is more likely that the antibody and the epitope will bind or stay bound together. An antibody with a $K_D$ of "no more than" a certain amount means that the antibody will bind to the epitope with the given $K_D$, or more strongly (or tightly).

While $K_D$ describes the binding characteristics of an epitope and an antibody, "potency" describes the effectiveness of the antibody itself for a function of the antibody. A relatively low $K_D$ does not automatically mean a high potency. Thus, antibodies can have a relatively low $K_D$ and a high potency (e.g., they bind well and alter the function strongly), a relatively high $K_D$ and a high potency (e.g., they don't bind well but have a strong impact on function), a relatively low $K_D$ and a low potency (e.g., they bind well, but not in a manner effective to alter a particular function) or a relatively high $K_D$ and a low potency (e.g., they simply do not bind to the target well). In one embodiment, high potency means that there is a high level of inhibition with a low concentration of antibody. In one embodiment, an antibody is potent or has a high potency when its $IC_{50}$ is a small value, for example, 130-110, 110-90, 90-60, 60-30, 30-25, 25-20, 20-15, or less pM.

"Substantially," unless otherwise specified in conjunction with another term, means that the value can vary within the amount that is attributable to errors in measurement that can occur during the creation or practice of the embodiments. "Significant" means that the value can vary as long as it is sufficient to allow the claimed invention to function for its intended use.

The term "selectively binds" in reference to an antibody does not mean that the antibody only binds to a single substance. Rather, it denotes that the $K_D$ of the antibody to a first substance is less than the $K_D$ of the antibody to a second substance. Antibodies that exclusively bind to an epitope only bind to that single epitope.

The term "and/or" denotes 1) including all of the relevant options, 2) including only one (or a subset) of a number of alternative options, 3) including both of the previous descriptions 1) or 2, and 4) including only one of the previous descriptions (1) or 2)).

The term "treat" or "treatment" refer to both therapeutic treatment and prophylactic or preventative measures, wherein the object is to prevent or slow down (lessen) an undesired physiological change or disorder, such as the development or spread of cancer or asthma.

The term "patient" includes human and veterinary subjects.

"Administer," for purposes of treatment, means to deliver to a patient. For example and without limitation, such delivery can be intravenous, intraperitoneal, by inhalation, intramuscular, subcutaneous, oral, topical, transdermal, or surgical.

"Therapeutically effective amount," for purposes of treatment, means an amount such that an observable change in the patient's condition and/or symptoms could result from its administration, either alone or in combination with other treatment. As discussed herein, and as will be appreciated by one of skill in the art, there are a variety of ways in which an effective amount can be determined. For example, an effective amount can be an amount required to reduce the amount of a biomarker by any significant amount, including, for example, 0-1, 1-5, 5-10, 10-20, 20-30, 30-40, 40-50, 505-60, 60-70, 70-80, 80-90, 90-95, 95-99, 99-100% of a reduction in the biomarker.

An "chondroitin sulfate related disorder" is any disease, disorder, or similar such term in which chondroitin sulfate regulates, influences or plays some role in the disease, optionally including the symptoms of the disease. For example, chondroitin sulfate may play a role in modulating the binding of a chondroitin sulfate binding protein to another protein, where the binding is associated with the disease or disorder. Examples include neurological disorders, including Parkinson's Disease, Alzheimer's Disease, Huntington's Disease, arthritis and trauma, such as spinal cord injury. In some embodiments, a "chondroitin sulfate dependent disorder" is any of the above that can be directly influenced by the administration of an antibody to chondroitin sulfate. For example, the disorder may be directly the result of excessive amounts of chondroitin sulfate or the activity of a CS binding protein. In some embodiments, a chondroitin sulfate antibody treatable disorder is any of the above that can be effectively treated by the addition of one of the presently disclosed antibodies.

Altering "chondroitin sulfate related activity" can include treating any of the above disorders with an antibody; it can also include other, nontherapeutic or prophylactic uses of the antibody which can alter the activity of chondroitin sulfate. In some embodiments, "chondroitin sulfate related disorder" can encompass any disorder in which an elevated level of chondroitin sulfate is present in the patient. In some embodiments, "chondroitin sulfate related disorder" can encompass any disorder that has a phenotype that is characteristic of chondroitin sulfate. Phenotypes that are characteristic of a patient with a chondroitin sulfate related disorder can be determined and observed by administering an amount of chondroitin sulfate to a patient to induce various phenotypes. The amount of chondroitin sulfate administered can vary and can be routinely determined by one of skill in the art.

A "pharmaceutically acceptable vehicle," for the purposes of treatment, is a physical embodiment that can be administered to a patient. Pharmaceutically acceptable vehicles can be, but are not limited to, pills, capsules, caplets, tablets, orally administered fluids, injectable fluids, sprays, aerosols, lozenges, neutraceuticals, creams, lotions, oils, solutions, pastes, powders, vapors, or liquids. One example of a pharmaceutically acceptable vehicle is a buffered isotonic solution, such as phosphate buffered saline (PBS).

"Neutralize," for purposes of treatment, means to partially or completely suppress chemical and/or biological activity.

"Down-regulate," for purposes of treatment, means to lower the level of a particular target.

"Mammal" for purposes of treatment refers to any animal classified as a mammal, including humans, domestic and farm animals, and zoo, sports, or pet animals, such as monkeys, dogs, horses, cats, cows, etc.

Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991).

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. (See generally, *Fundamental Immunology* Ch. 7 (Paul, W., ed., 2nd ed. Raven Press, N.Y. (1989)), incorporated by reference in its entirety for all purposes). The variable regions of each light/heavy chain pair form the antibody binding site.

Thus, an intact antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J. Mol. Biol.* 196:901-917 (1987); Chothia et al. *Nature* 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. (See, e.g., Songsivilai & Lachmann *Clin. Exp. Immunol.* 79: 315-321 (1990), Kostelny et al. *J. Immunol.* 148:1547-1553 (1992)). Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Preparation of CS Tetrasaccharides

FIG. 1 show an embodiment of a chemical synthetic scheme to generate oligosaccharides representing three major subclasses of CS found in vivo, CS-A, CS-C, and CS-E. Tetrasulfated molecule 1 displays the CS-E sulfation sequence, a motif enriched in the developing brain and associated with the proteoglycans appican, syndecan-1 and -4, neuroglycan C and phosphacan. Disulfated molecules 2 and 3 represent the most abundant sulfation patterns in vivo, CS-C and CS-A, respectively. For comparison, tetrasulfated oligosaccharide 4, denoted CS-R, was also synthesized. CS-R possesses the same overall negative charge as 1 but has sulfate groups installed at the C-2 and C-3 positions of D-glucuronic acid (GlcA).

The synthetic route disclosed in FIG. 1 allows for the generation of various CS sulfation motifs from a core disaccharide building block 5. Stereocontrol in the glycosylation reactions to form β-linked oligosaccharides was achieved using α-trichloroacetimidate donors containing C-2 N-trichloroacetyl (TCA) or O-benzoyl (Bz) participating groups. An orthogonal protecting group strategy was developed to install the specific sulfation sequences. In particular, p-methoxybenzylidene and Bz groups were used to mask positions that were exposed at late stages of the synthesis for sulfation. To elongate the carbohydrate chain, a silyl ether was used to protect the C-4 position of GlcA and liberate a hydroxyl group nucleophile for reaction with a glycosylating agent. Finally, a versatile chemical handle, the allyl moiety, was appended to the reducing end of the oligosaccharides for convenient conjugation to proteins, small molecules and surfaces.

The core disaccharide building block was synthesized on a multi-gram scale from protected monosaccharides 6 and 7. For elongation of the carbohydrate chain, the disaccharide was readily converted to a suitable glycosyl donor and acceptor pair (8 and 9). Silyl deprotection of 5 using HF.pyridine followed by coupling to activated imidate 8 delivered the β-linked tetrasaccharide 10 with excellent stereoselectivity.

Radical-mediated conversion of the TCA to an N-acetyl group and oxidative cleavage of the p-methoxybenzylidene acetal afforded the key tetraol intermediate 11. Sulfation of 11 under vigorous conditions generated the precursor to CS-E and under mild conditions yielded the precursor to CS-C. The target CS-E and CS-C tetrasaccharides (1 and 2, respectively) were obtained after silyl deprotection and saponification. Synthesis of the CS-A tetrasaccharide 3 was achieved by selective benzoylation of the C-6 hydroxyl groups using benzoyl cyanide, followed by sulfation at the C-4 position. The remaining silyl and ester protecting groups were removed as described previously to afford 3. Finally, tetrasulfated 4 was generated through formation of the benzylidene acetal, which proved more stable than the p-methoxybenzylidene acetal during the sulfation reaction. Following saponification, the resulting free hydroxyl groups were sulfated and the desired CS-R tetrasaccharide obtained after deprotection of the remaining protecting groups under mildly acidic conditions. Tetrasaccharides 1-4 were purified by size-exclusion chromatography and their structures confirmed by $^1$H-NMR, proton decoupling experiments, and electrospray ionization mass spectrometry (ESI).

Preparation of Antibodies

For the production of anti-CS antibodies, various host animals can be immunized by injection with one or more chondroitin sulfate polysaccharides, preferably homogeneous CS-A, CS-C or CS-E. Such host animals can include but are not limited to rabbits, mice, and rats, to name but a few. Various adjuvants can be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495-497; and U.S. Pat. No. 4,376,110), the human B-cell hybridoma technique (Kosbor et al., 1983 *Immunology Today* 4:72; Cole et al., 1983 *Proc Natl Acad Sci USA* 80:2026-2030), and the EBV-hybridoma technique (Cole et al., 1985 in *Monoclonal Antibodies And Cancer Therapy*, Alan R. Liss, Inc., pp. 77-96). Such antibodies can be of any immunoglobulin class including IgG, IgM, IgE, IgA., IgD and any subclass thereof. The hybridoma producing the mAb of this invention can be cultivated in vitro or in vivo. Production of high titers of mAbs in vivo makes this the presently preferred method of production. An example of anti-chondroitin sulfate antibody production is provided in the Examples section below.

Anti-CS antibodies were prepared as described in the Examples section below. Briefly, one or more homogeneous chondroitin sulfate polysaccharides were conjugated to bovine serum albumin (BSA) or keyhole limpet hemocyanin (KLH). The CS-protein conjugates were then dialyzed, and the protein concentrations were determined. Mice were immunized with the CS-KLH conjugate and boosted five times over a period of 2 months. Spleen cells of the mice were fused to a myeloma cell line, and multiclonal cell lines were then screened via ELISA analysis. Clones specific for the desired CS tetrasaccharide and with absorbance values greater than 1.0 were kept for subsequent expansion. Single cell clones were then screened via ELISA, and clones specific for the desired CS tetrasaccharide and with absorbance values greater than 1.0 were analyzed by dot blot analysis. Antibodies to CS preferably are able to bind specifically to a single subtype of CS.

The genetic material that encodes an antibody that specifically binds chondroitin sulfate can be isolated, and that material can be introduced into a suitable expression vector and thereafter transfected into host cells. Thus, anti-CS antibodies can be expressed in cell lines other than hybridoma cell lines. Sequences encoding particular antibodies can be used for transformation of a suitable mammalian host cell, such as a CHO cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740, 461, and 4,959,455 (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. Cell lines of particular preference are selected through determining which cell lines have high expression levels and produce antibodies with chondroitin sulfate binding properties.

The invention also includes functional equivalents of the antibodies described in this specification. Functional equivalents have binding characteristics that are comparable to those of the antibodies, and include, for example, chimerized, humanized and single chain antibodies as well as fragments thereof. Methods of producing such functional equivalents are disclosed in PCT Application WO 93/21319, European Patent Application No. 239,400; PCT Application WO 89/09622; European Patent Application 338,745; and European Patent Application EP 332,424.

Functional equivalents include polypeptides with amino acid sequences substantially the same as the amino acid sequence of the variable or hypervariable regions of the antibodies of the invention. "Substantially the same" as applied to an amino acid sequence is defined herein as a sequence with at least 80%, preferably at least about 90%, and more preferably at least about 95% sequence identity to another amino acid sequence, as determined by the FASTA search method in accordance with Pearson and Lipman, Proc. Natl. Acad. Sci. USA 85, 2444 2448 (1988).

In addition, techniques developed for the production of "chimeric antibodies" (Morrison et al. 1984 *Proc Natl Acad Sci USA* 81:6851-6855; Neuberger et al. 1984 *Nature* 312: 604-608; Takeda et al. 1985 *Nature* 314:452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Chimerized antibodies preferably have constant regions derived substantially or exclusively from human antibody constant regions and variable regions derived substantially or exclusively from the sequence of the variable region from a mammal other than a human.

Humanized forms of the antibodies can be made by methods known in the art, for example by substituting the complementarity determining regions of, for example, a mouse antibody, into a human framework domain, e.g., see PCT Pub. No. WO92/22653. Humanized antibodies preferably have constant regions and variable regions other than the complement determining regions (CDRs) derived substantially or exclusively from the corresponding human antibody regions and CDRs derived substantially or exclusively from a mammal other than a human.

Functional equivalents also include single-chain antibody fragments, also known as single-chain antibodies (scFvs). Single-chain antibody fragments of the present invention are recombinant polypeptides which bind CS epitopes. These fragments contain at least one fragment of an antibody variable heavy-chain amino acid sequence (VH) tethered to at least one fragment of an antibody variable light-chain sequence (VL) with or without one or more interconnecting linkers. Such a linker may be a short, flexible peptide selected to assure that the proper three-dimensional folding of the (VL) and (VH) domains occurs once they are linked so as to maintain the target molecule binding-specificity of the whole antibody from which the single-chain antibody fragment is derived. Generally, the carboxyl terminus of the (VL) or (VH) sequence may be covalently linked by such a peptide linker to the amino acid terminus of a complementary (VL) and (VH) sequence. Single-chain antibody fragments may be generated by molecular cloning, antibody phage display library or similar techniques. These proteins may be produced either in eukaryotic cells or prokaryotic cells, including bacteria.

Single-chain antibody fragments contain amino acid sequences having at least one of the variable or complementarity determining regions (CDR's) of the whole antibodies described in this specification, but are lacking some or all of the constant domains of those antibodies. These constant domains are not necessary for antigen binding, but constitute a major portion of the structure of whole antibodies. Single-chain antibody fragments may therefore overcome some of the problems associated with the use of antibodies containing a part or all of a constant domain. For example, single-chain antibody fragments tend to be free of undesired interactions between biological molecules and the heavy-chain constant region, or other unwanted biological activity. Additionally, single-chain antibody fragments are considerably smaller than whole antibodies and may therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely to provoke an immune response in a recipient than whole antibodies.

Functional equivalents further include fragments of antibodies that have the same, or comparable binding characteristics to those of the whole antibody. Antibody fragments which recognize specific epitopes can be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries can be constructed (Huse et al., 1989 *Science* 246:1275-1281) to allow rapid and easy identification of monoclonal Fab fragments with the desired specificity. In some embodiments, the antibody fragments contain all six complement determining regions of the whole antibody, although fragments containing fewer than all of such regions, such as three, four or five CDRs, are also functional. Further, the functional equivalents may be or may combine members of any one of the following immunoglobulin classes: IgG, IgM, IgA, IgD, or IgE, and the subclasses thereof.

Techniques described for the production of single chain antibodies (U.S. Pat. No. 4,946,778; Bird 1988 *Science* 242: 423-426; Huston et al. 1988 *Proc Natl Acad Sci USA* 85:5879-5883; and Ward et al. 1989 *Nature* 334:544-546) can be adapted to produce single chain antibodies against chondroitin sulfate gene products. Single chain antibodies can be formed by linking the heavy and light chain fragments of the Fv region via an amino acid bridge, resulting in a single chain polypeptide.

Human Antibodies and Humanization of Antibodies

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of human antibody function into a rodent so that the rodent produces fully human antibodies. Unless specifically identified herein, "human" and "fully human" antibodies can be used interchangeably herein. The term "fully human" can be useful when distinguishing antibodies that are only partially human from those that are completely, or fully human.

Fully human antibodies can be made by any methods known in the art. One method for generating fully human antibodies is through the use of XENOMOUSE® strains of mice which have been engineered to contain 245 kb and 190 kb-sized germline configuration fragments of the human heavy chain locus and kappa light chain locus. See Green et al. *Nature Genetics* 7:13-21 (1994). The XENOMOUSE® strains are available from Abgenix, Inc. (Fremont, Calif.).

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more DH genes, one or more $J_H$ genes, a mu constant region, and a second constant region (preferably a gamma constant region) are formed into a construct for insertion into an animal.

Diagnostic Applications

The anti-CS antibodies can be employed in any known assay method, such as competitive binding assays, direct and indirect sandwich assays, and immunoprecipitation assays (Zola, Monoclonal Antibodies: A Manual of Techniques, pp. 147-158 (CRC Press, Inc., 1987)). In some embodiments, the anti-CS antibodies can be used to detect CS in a biological sample in vitro or in vivo. In some embodiments, the anti-CS antibodies can be used in a conventional immunoassay, including, without limitation, an ELISA, an RIA, FACS, tissue immunohistochemistry, Western blot or immunoprecipitation. In some embodiments, the anti-CS antibodies of the invention may be used to detect CS from humans. In some embodiments, the anti-CS antibodies can be used to detect CS from Old World primates such as cynomologous and rhesus monkeys, chimpanzees and apes.

For diagnostic applications, the anti-CS antibodies can be labeled with a detectable moiety. The detectable moiety can be any one which is capable of producing, either directly or indirectly, a detectable signal. Suitable labels for the antibody or secondary can include various enzymes, prosthetic groups, fluorescent materials, luminescent materials, magnetic agents and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include luciferin, umbelliferone, fluorescein, fluorescein isothiocyanate, rhodamine, dichlorotriazinylamine fluorescein, dansyl chloride or phycoerythrin; an example of a luminescent material includes luminol; an example of a magnetic agent includes gadolinium; and examples of suitable radioactive material include $^{125}$I, $^{131}$I, $^{35}$S, $^{14}$C, $^{32}$P, or $^{3}$H.

Any method known in the art for conjugating the antibody to the detectable moiety may be employed, including those methods described by Hunter, et al., *Nature* 144:945 (1962); David, et al., *Biochemistry* 13:1014 (1974); Pain, et al., *J. Immunol. Meth.* 40:219 (1981); and Nygren, *J. Histochem. and Cytochem.* 30:407 (1982).

Methods for detecting anti-CS in a biological sample are disclosed in accordance with some embodiments of the present invention. Such methods can comprise contacting a biological sample with an anti-CS antibody of the invention and detecting the bound antibody bound to anti-CS, to detect the CS in the biological sample. In some embodiments, the anti-CS antibody can be directly labeled with a detectable label. In another embodiment, the anti-CS antibody (the first antibody) can be unlabeled and a second antibody or other molecule that can bind the anti-CS antibody is labeled. As is well known to one of skill in the art, a second antibody is chosen that is able to specifically bind the specific species and class of the first antibody. For example, if the anti-CS antibody is a human IgG, then the secondary antibody may be an anti-human-IgG. Other molecules that can bind to antibodies include, without limitation, Protein A and Protein G, both of which are available commercially, e.g., from Pierce Chemical Co.

In some embodiments, CS can be assayed in a biological sample by a competition immunoassay utilizing CS standards labeled with a detectable substance and an unlabeled anti-CS antibody. In this assay, the biological sample, the labeled CS standards and the anti-CS antibody are combined and the amount of labeled CS standard bound to the unlabeled antibody is determined. The amount of CS in the biological sample is inversely proportional to the amount of labeled CS standard bound to the anti-CS antibody.

One may use the immunoassays disclosed above for a number of purposes. In some embodiments, the anti-CS antibodies may be used to detect CS in cells in cell culture. In some embodiments, the anti-CS antibodies may be used to determine the level of sulfation, and/or the amount of CS on the cell surface after treatment of the cells with various compounds. This method can be used to test compounds that may be used to activate or inhibit CS. In this method, one sample of cells is treated with a test compound for a period of time while another sample is left untreated. The CS level can be measured using an immunoassay.

An immunoassay for determining cell surface levels of CS typically includes the steps of labeling the cell surface proteins with a detectable label, such as biotin or $^{125}$I, immunoprecipitating the CS-bound cells with an anti-CS antibody and then detecting the labeled CS. Mother preferred immunoassay for determining the localization of CS, e.g., cell surface levels, is by using immunohistochemistry. Methods such as ELISA, RIA, Western blot, immunohistochemistry, cell surface labeling of integral membrane proteins and immunoprecipitation are well known in the art. See, e.g., Harlow and Lane, Antibodies: A Laboratory Manual, New York: Cold Spring Harbor Press, 1990.

The anti-CS antibodies of the invention can also be used to determine the levels of CS in a tissue or in cells derived from the tissue. In some embodiments, the tissue can be a diseased or injured tissue, which can be excised from the patient and used in an immunoassay to determine, e.g., CS levels, cell surface levels of CS or localization of CS by the methods discussed above. The method can be used to determine if a tissue expresses CS at a high level.

The above-described diagnostic method can be used to determine the level of expression of CS in a tissue, which may be indicative, for example, of a disease or disorder, the state of a disease or disorder, or that the tissue will respond well to treatment with anti-CS antibody.

The antibodies of the present invention may also be used in vivo to localize tissues and organs that express CS. In some embodiments, the anti-CS antibodies can be used localize CS-expressing cells. An advantage of some of the anti-CS antibodies of the present invention is that they are highly specific for a particular CS, preferably a CS tetrasaccharide. In some embodiments, the method can comprise the steps of administering an anti-CS antibody or a pharmaceutical composition thereof to a patient in need of such a diagnostic test and subjecting the patient to imaging analysis determine the location of the CS-expressing tissues. Imaging analysis is well known in the medical art, and includes, without limitation, x-ray analysis, magnetic resonance imaging (MRI) or computed tomography (CE). In another embodiment of the method, a biopsy is obtained from the patient to determine whether the tissue of interest expresses CS rather than subjecting the patient to imaging analysis. In some embodiments, the anti-CS antibodies may be labeled with a detectable agent that can be imaged in a patient. For example, the antibody may be labeled with a contrast agent, such as barium, which can be used for x-ray analysis, or a magnetic contrast agent, such as a gadolinium chelate, which can be used for MRI or CE. Other labeling agents include, without limitation, radioisotopes, such as $^{99}$Tc. In another embodiment, the anti-CS antibody will be unlabeled and will be imaged by administering a second antibody or other molecule that is detectable and that can bind the anti-CS antibody.

In some embodiments, the anti-CS antibodies can be useful as affinity purification agents. In this process, the antibodies are immobilized on a suitable support, such as Sephadex resin or filter paper, using methods well known in the art.

Antibody Therapeutics

Anti-CS antibodies have therapeutic value for treating symptoms and conditions related to chondroitin sulfate activity (e.g., a chondroitin sulfate related disorder). In some embodiments, the anti-CS antibodies disclosed herein are used in the diagnosis, prevention or treatment of neurological disorders, including Parkinson's Disease, Alzheimer's Disease, Huntington's Disease, arthritis and trauma, such as spinal cord injury.

In some embodiments, the use of the antibodies in a medicament for the treatment of a chondroitin sulfate related disorder (a disease, condition, etc., relating to chondroitin sulfate) is contemplated. The medicament can contain a therapeutically effective amount of the antibody. In some embodiments, the amount of chondroitin sulfate antibody in the medicament is sufficient so that at least one beneficial result is observed, e.g., a lessening of a symptom. In some embodiments, the amount that is administered removes all of the symptoms of the chondroitin sulfate related disorder. In some embodiments, the amount is sufficient so that the level of a biomarker decreases in a subject after the medicament has been administered. In some embodiments, the amount of the antibody administered is about 0.001 to 1000, 0.1 to 100, 0.5 to 50, 1 to 10, 1, 3, or 10 mg of antibody/kg of subject. As will be appreciated by one of skill in the art, the actual amount of the antibody can depend upon the particular disorder (e.g., asthma, is it acute or chronic), the method of administration, the frequency of administration, the desired result, the characteristics of the patient, and the characteristics of the antibody. As will be appreciated by one of skill in the art, the use of the antibody in the preparation or manufacture of a medicament can involve any of the disclosed antibodies in any amount, sufficient to treat the particular condition it is directed to. Any of the herein disclosed conditions, or any chondroitin sulfate related disorders, can be the condition to be treated. In some embodiments, a medicament is prepared with one of the monoclonal antibodies (mAb) selected from the group consisting of ant-CS-C antibody 5D2-1D2, anti-CS-E antibody 2D11-2A10 and anti-CS-A antibody 1009-2B5.

As will be appreciated by one of skill in the art, the nature of the disorder can play a role in the amount, frequency, and method of administration. For example, in chronic disorders, relatively larger amounts, more potent antibodies, and/or more frequently administered doses of the antibody can be required. Similarly, in acute disorders, the amount of antibody required for treatment, including prophylaxis, can be relatively less. In subjects in which sensitization is initially required prior to the challenge, lower amounts of the antibody can be beneficial compared to the amount required for subjects that are naturally allergic. In such chronic systems, increased amounts of the antibody, as well as increased frequency of administration can be advantageous. The exact amount can readily be determined by one of skill in the art, in light of the present disclosure. One of skill in the art will further appreciate other factors and how to adjust the administration of the antibody accordingly.

If desired, the isotype of an anti-CS antibody can be switched, for example to take advantage of a biological property of a different isotype. For example, in some circumstances it can be desirable for the therapeutic antibodies against chondroitin sulfate to be capable of fixing complement and participating in complement-dependent cytotoxicity (CDC). There are a number of isotypes of antibodies that are capable of the same, including, without limitation, the following: murine IgM, murine IgG2a, murine IgG2b, murine IgG3, human IgM, human IgG1, and human IgG3. It will be appreciated that antibodies that are generated need not initially possess such an isotype but, rather, the antibody as generated can possess any isotype and the antibody can be isotype switched thereafter using conventional techniques that are well known in the art. Such techniques include the use of direct recombinant techniques (see e.g., U.S. Pat. No. 4,816,397), cell-cell fusion techniques (see e.g., U.S. Pat. Nos. 5,916,771 and 6,207,418), among others.

In some embodiments, the anti-CS antibodies discussed herein are mouse antibodies. In some embodiments, the anti-CS antibodies discussed herein can be human antibodies. If an antibody possessed desired binding to chondroitin sulfate, it could be readily isotype switched to generate a human IgM, human IgG1, or human IgG3 isotype, while still possessing the same variable region (which defines the antibody's specificity and some of its affinity). Such molecule would then be capable of fixing complement and participating in CDC.

In the cell-cell fusion technique, a myeloma or other cell line is prepared that possesses a heavy chain with any desired isotype and another myeloma or other cell line is prepared that possesses the light chain. Such cells can, thereafter, be fused and a cell line expressing an intact antibody can be isolated.

Accordingly, as antibody candidates are generated that meet desired "structural" attributes as discussed above, they can generally be provided with at least certain of the desired "functional" attributes through isotype switching.

Biologically active antibodies that bind chondroitin sulfate are preferably used in a sterile pharmaceutical preparation or formulation to reduce the activity of chondroitin sulfate. Anti-CS antibodies preferably possess adequate affinity to potently interfere with the binding of chondroitin sulfate to a chondroitin sulfate binding protein. For example, the antibody can prevent interaction of CS-E with tumor necrosis factor-α (TNF-α).

When used for in vivo administration, the antibody formulation is preferably sterile. This is readily accomplished by any method know in the art, for example by filtration through sterile filtration membranes. The modality of antibody administration is in accord with known methods.

EXAMPLES

The following examples are by way of illustration and not by way of limitation.

Example 1

CS Microarray Development

This example illustrates development of CS microarrays.

To create the microarrays, a general, highly efficient strategy was developed to attach synthetic oligosaccharides to the array surface. The preparation of CS tetrasaccharides is described above. CS molecules displaying different sulfation sequences were synthesized with an allyl functionality on the reducing end of the sugar. This group is stable to the chemical manipulations used to synthesize the oligosaccharides, yet it can be readily functionalized for surface conjugation. Ozonolysis of CS-A tetrasaccharide, CS-C tetrasaccharide, CS-E tetrasaccharide and CS-E disaccharide, followed by treatment with 1,2-(bisaminooxy)ethane furnished CS oligosaccharides with a convenient aminooxy handle for covalent attachment to aldehyde-coated glass slides. Solutions of the aminooxy oligosaccharides in 300 mM $NaH_2PO_4$, pH 5.0 (10 µL/well in a 384-well plate) were arrayed on Hydrogel Aldehyde slides (NoAb Biodiscoveries) by using a Microgrid 11 arrayer (Biorobotics) to deliver sub-nanoliter volumes at room temperature and 50% humidity. Concentrations of carbohydrates ranged from 0-500 µM. The resulting arrays were incubated in a 70% humidity chamber at room temperature overnight and then stored in a low humidity, dust-free dessicator. Additional details for the development of the glycosaminoglycan microarrays are provided in the following references: Tully, S. E. et al., *J. Am. Chme. Soc.* (2006) 128: 7740-7741; Gama, C. I. et al., *Nature Chemical Biology* (2006) 2(9):467-473; Shipp, E. L. and Hsieh-Wilson, L. C., *Chemistry & Biology* (2007) 14:195-208; each of which is incorporated herein by reference in its entirety.

Importantly, this strategy requires minimal manipulation of the sulfated oligosaccharides, enabling their direct conjugation in two short, high-yielding steps. Moreover, the approach is compatible with standard DNA robotic printing and fluorescence scanning technology, which requires only minimal amounts of material and allows a large number of molecular interactions to be probed simultaneously.

Example 2

Chondroitin Sulfate Antibody Preparation

This example illustrates the preparation of anti-CS antibodies.

CS tetrasaccharides prepared as described above were conjugated to bovine serum albumin (BSA) or keyhole limpet hemocyanin (KLH) as follows. Ozonolysis of the anomeric allyl group of the CS-A, —C, and -E tetrasaccharides (0.51 µmol) was followed by treatment of each compound with BSA (0.34 mg, 0.0051 µmol) or KLH (0.44 mg, 0.0063 µmol) and NaCNBH$_3$ (0.5 mg) in H$_2$O (pH 9.5 using K$_2$CO$_3$) for 2 d at room temperature (RT). The CS-protein conjugates were then exhaustively dialyzed against 0.01 M Na$_2$HPO$_4$, 0.15 M NaCl, pH 7.4 at 4° C., and the protein concentrations were determined using the BCA assay (Pierce). The epitope density was determined by comparing the conjugated to the unconjugated proteins using the Habeeb assay (Shi, R.-X.; Ong, C.-N.; Shen, H.-M. *Oncogene* 2004, 23, 7712-7721). In short, 0.1% trinitrobenzenesulfonic acid (50 µL) and 4% NaHCO$_3$, pH 9.5 (50 µL) were added to the protein solution (10 µL) in PBS (40 µL). The mixture was incubated at 40° C. for 2 h, quenched with 10% SDS (50 µL), 1 M HCl (25 µL), and H$_2$O (500 µL), and the absorbance at 363 nm was measured. The epitope densities for the conjugates were: CS-A-BSA conjugate=14, CS-C-BSA conjugate=16, CS-E-BSA conjugate=14, CS-A-KLH conjugate=15, CS-C-KLH conjugate=15 and CS-E-KLH conjugate=14.

For the preparation of CS-A and CS-E antibodies, Balb/c mice were immunized with CS-A and CS-E tetrasaccharides conjugated to keyhole limpet hemocyanin (KLH) as described above. Three Balb/c female mice, 4-6 weeks old, were primed and boosted at 2-week intervals for a total of 5 intraperitoneal injections (5 mg per injection). CS-A- or CS-E-KLH conjugates were mixed with RIBI™ adjuvant (RIBI Immunochem) for the first two injections, and a final series of 3 boosts was performed without adjuvant. Bleeds were taken 1 week after each injection and monitored by dot blot analysis. The most responsive mouse was boosted and sacrificed after three days. Spleen cells were fused with HL-1 murine myeloma cells (Ventrex) using polyethylene glycol (PEG 1500, Boehringer-Mannheim). Multiclonal and monoclonal cell lines were then screened via ELISA analysis. A number of CS-A and CS-E antibodies were thus identified, including the CS-A antibody 10G9-2B5 and the CS-E antibody 2D11-2A10.

For the preparation of CS-C antibodies, mice were immunized with the CS-C-KLH conjugate and boosted five times over a period of 2 months with 50 µs of the conjugate at each boost. The final boost was performed 3 d before fusion of the spleen cells to a myeloma cell line. Multiclonal cell lines were then screened via ELISA analysis. The BSA conjugates (1 µg/mL in 50 mM Na$_2$CO$_3$, pH 9.6) were added to a 384-well NUNC Maxisorp clear plate (25 µL per well), and the plate was sealed and incubated for 12 h at 4° C. The wells were aspirated, washed four times with PBS containing 0.05% TWEEN-20 (PBST, 75 µL/wash), and blocked for 2 h at RT with 10% horse serum (Gibco) in PBS (75 µL). After the blocking step, the plate was washed four times with PBST, and the supernatants from the antibody producing cultures (25 µL) were added to the wells and incubated at room temperature for 2 h. Following aspiration, the wells were washed four times with PBST and treated with a horseradish peroxidase (HRP)-conjugated goat anti-mouse antibody (Pierce; 1:10,000, 25 µL/well) in blocking buffer for 1 h at RT. The wells were again aspirated, washed four times with PBST, and then developed with ABTS liquid substrate solution (Sigma; 25 µL/well, solution at RT) for 30 min at RT. Color development was monitored on a VICTOR plate reader (PerkinElmer) at 405 nm. Only clones specific for the CS-C tetrasaccharide and with absorbance values greater than 1.0 were kept for subsequent expansion. Single cell clones were then screened via ELISA as previously described, and clones specific for the CS-C tetrasaccharide and with absorbance values greater than 1.0 were analyzed by dot blot analysis. A number of CS-C antibodies were thus identified, including CS-C antibody 5D2-1D2.

Example 3

Specificity of Anti-CS Antibodies

This example illustrates specificity of CS antibodies using the CS microarray and dot blot analysis.

Figure 2:
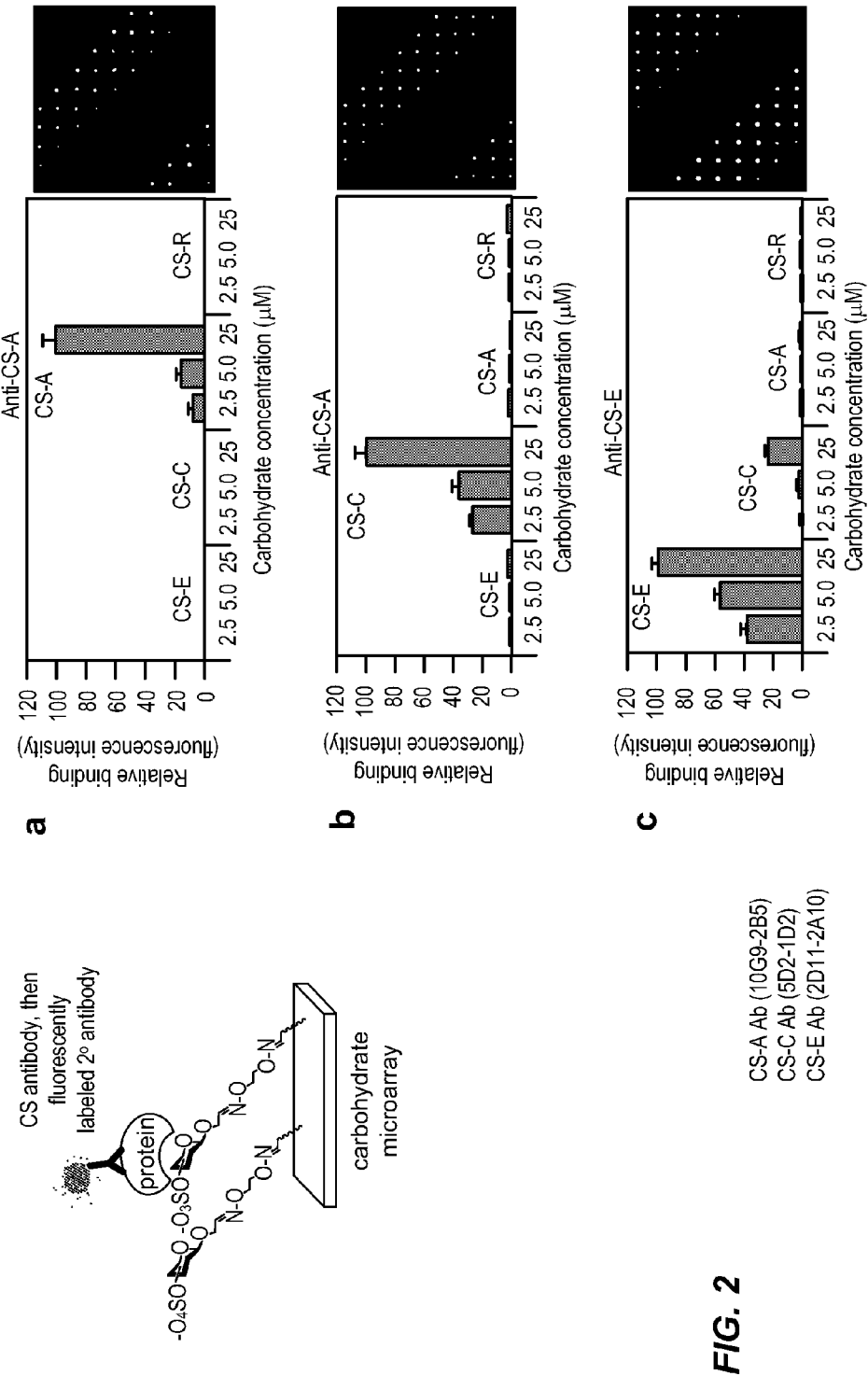
FIG. 2 shows the selectivity of CS antibodies for distinct sulfation motifs based on binding to tetrasaccharide microarrays.

The CS microarray prepared as described in Example 1 were treated with NaBH$_4$ prior to use to quench unreacted aldehyde groups. The microarrays were then incubated with monoclonal antibodies raised against CS-A, CS-C or CS-E tetra-saccharide conjugated to keyhole limpet hemocyanin, and antibody binding was visualized using a secondary Cy3-conjugated goat anti-mouse antibody. The CS-A antibody 10G9-2B5 bound to the CS-A tetrasaccharide in a concentration-dependent manner, and strong selectivity for the CS-A motif was observed, with little detectable binding to the CS-C or CS-E sulfation motifs, as shown in FIG. 2. Similarly, the CS-E antibody 2D11-2A10 selectively recognized the CS-E tetrasaccharide and displayed only weak binding to the CS-C motif at high tetrasaccharide concentrations, while the CS-C antibody 5D2-1D2 selectively recognized CS-C and did not display any appreciable binding to CS-E or CS-A (FIG. 2). To examine the carbohydrate chain length required for interaction, the ability of the CS-E antibody to bind CS-E di- and tetrasaccharides was compared. The CS-E disaccharide showed significantly reduced antibody binding, indicating a clear preference of the antibody for tetrasaccharide epitopes.

The antibody specificities obtained from the microarray were confirmed by traditional dot blot analyses. CS-A tetrasaccharide, CS-C tetrasaccharide and CS-E tetrasaccharide were covalently attached to bovine serum albumin (BSA) by oxidation to the corresponding aldehydes, followed by reductive amination to link the carbohydrates to lysine residues of the protein. The CS-BSA conjugates were spotted onto nitrocellulose membranes and incubated with the CS-A (10G9-2B5) or CS-E (2D11-2A10) antibody. Antibody binding was visualized by chemiluminescence using a secondary goat anti-mouse antibody conjugated to horseradish peroxidase. Consistent with the microarray data, highly selective binding of the antibodies to their respective sulfated antigens was observed.

Example 4

Method of Detecting CS in a Biological Sample

CS polypeptides can be detected in a biological sample, and if an increased or decreased level of CS is detected, the respective CS is a marker for a particular phenotype. Methods of detection are numerous, and thus, it is understood that one skilled in the art can modify the following assay to fit their particular needs.

For example, antibody-sandwich ELISAs are used to detect CS in a sample, preferably a biological sample. Wells of a microtiter plate are coated with specific antibodies to CS, respectively, at a final concentration of 0.2 to 10 ug/ml. The wells are blocked so that non-specific binding of CS to their respective well is reduced.

The coated wells are then incubated with a sample containing CS. Preferably, serial dilutions of the sample should be used to validate results. The plates are then washed to remove unbounded CS.

Next, specific anti-CS antibody-alkaline phosphatase conjugate is added and incubated. The plates are again washed to remove unbounded conjugate.

A substrate solution is added to each well and incubated for the appropriate development time. The reaction can then be measured by a microtiter plate reader. A standard curve is prepared using serial dilutions of a control sample, and the CS polypeptide concentration of a sample can be determined using the standard curve.

Example 5

The CS-E Sulfation Motif Stimulates Neuronal Growth

This example illustrates specificity of CS-E stimulation of neuronal growth.

Neuritogenic activity of CS-A tetrasaccharide, CS-C tetrasaccharide and CS-E tetrasaccharide was compared using neuronal cultures. Primary hippocampal neurons from embryonic day 18 (E 18) rats were cultured on coverslips coated with polyornithine and CS-A tetrasaccharide, CS-C tetrasaccharide, CS-E tetrasaccharide or CS-R tetrasaccharide. The neurons were fixed after 48 h, immunostained with anti-tubulin antibodies, and examined by confocal fluorescence microscopy.

Notably, a specific CS sulfation pattern was required for the neuritogenic activity of CS. Whereas the CS-E tetrasaccharide stimulated neurite outgrowth by 48.6±2.3% relative to the polyornithine control, tetrasaccharides representing other CS subclasses found in vivo, CS-A and CS-C, had no appreciable activity. Moreover, CS-R had no effect on neurite outgrowth, despite having the same overall negative charge as CS-E. Thus, altering the precise orientation of the sulfate groups has a critical impact on the growth-promoting ability of CS.

Dopaminergic neurons from the mesencephalon of rat embryos were cultured on a substratum of each tetrasaccharide. The CS-E tetrasaccharide had a similar activity toward both dopaminergic and hippocampal neurons, inducing the outgrowth of dopaminergic neurons by 29.6:1:6.0%. In contrast, the CS-C, CS-A and CS-R motifs exhibited no significant neuritogenic activity. Similarly, CS-E tetrasaccharide, but not other sulfation motifs, stimulated the outgrowth of dorsal root ganglion (ORO) neurons derived from the spinal cord.

To investigate whether CS recruits specific growth factors to the cell, hippocampal neurons were treated with the CS-E tetrasaccharide in the presence or absence of antibodies selective for midkine or BDNF. The antibodies were expected to block the interaction of the endogenous growth factors with the CSE substratum and thereby abolish the neuritogenic effects. Antibodies against midkine or BDNF had no effect on neurite outgrowth in the absence of the tetrasaccharide. Importantly, addition of either antibody blocked the neurite outgrowth induced by CS-E. In contrast, a control antibody selective for FGF-1 could not abolish the growth-promoting effects of CS-E.

As further confirmation, antibodies selective for the cell surface receptors, protein tyrosine phosphatase zeta (PTPζ) and tyrosine kinase B receptor (TrkB) were used. Binding of midkine and BDNF to PTPζ and TrkB, respectively, has been shown to promote neuronal outgrowth and survival in various systems by activating intracellular pathways such as mitogen associated protein kinase (MAPK), and phosphatidylinositol-3 kinase (PI3-K) pathways. Antibodies against either PTPζ or TrkB, but not TrkA, blocked the neuritogenic activity of CS-E. In contrast, neither antibody alone had an effect on neurite outgrowth. These results indicate that the CS-E sulfation motif stimulates neuronal growth through activation of midkine-PTPζ and BDNF-TrkB signaling pathways.

Coverslip preparation, hippocampal cultures and neurite outgrowth measurements were performed as described in Jacquinet, J.-C. et al., *Carbohydr. Res.* 314, 283-288 (1998), incorporated herein by reference in its entirety. DRG cultures were prepared from the spinal cord of E18 embryos of Sprague-Dawley rats. Ganglia were dissected in Calcium and Magnesium Free-Hanks Balanced Salt Solution [CMF-HBSS (Gibco)], digested with 0.25% trypsin (GibeD) for 20 min at 37° C., and dissociated in culture media consisting of DMEM-F12 (Gibco), 10% horse serum (GibeD), N2 supplement (Gibco), and NGF (50 ng/mL; Gibco). DRG neurons were plated at 100 cells/mm$^2$ on covers lips coated with poly-DL-ornithine and the tetrasaccharides (50 or 100 μg/mL). After 24 h, neurons were immunostained with an anti-tubulin III antibody (Sigma, 1:500) and examined by confocal fluorescence microscopy. Cells were imaged on a Zeiss Axiovert 100M inverted confocal microscope, and images were captured with LSM Pascal software. Mesencephalic cells were cultured on dishes coated with polyornithine and the tetrasaccharides (16 or 50 μg/mL) for 5 days, immunostained with an anti-tyrosine hydroxylase antibody (Pel-Freeze; 1:1,000), and examined by confocal fluorescence microscopy. The neurite length is expressed as total length of the neurite from the perikarya, and only cells with neurites longer than one cell body diameter were counted, as per standard protocol. The length of the longest neurite was measured using NTH Image 1.62 software. The mean neurite lengths were compared among the different substrate conditions by the ANOVA test followed by the Scheffe test using the statistical analysis program StatView (SAS Institute Inc.).

For the antibody treatments, hippocampal neurons were cultured on a substratum of poly-DL-ornithine in the presence or absence of CS-E tetrasaccharide (500 μg/mL). After 24 h, antibodies selective for midkine (Santa Cruz; 4 μg/mL), BDNF (Santa Cruz; 1 μg/ml), FGF-1 (R & D Systems; 4 μg/mL), PTPS (Santa Cruz; 2 μg/mL), TrkB (Santa Cruz; 1 μg/mL), or TrkA (Santa Cruz; 4 μg/mL) were added to the medium (500 μL). Neurons were cultured for an additional 24 h before immunostaining with an anti-tubulin antibody (Sigma; 1:500) and microscopy analysis. Relative concentrations of the CS tetrasaccharides were determined by measuring the uronic acid content using the carbazole reaction.

Example 6

Treatment of Spinal Cord Injury

This example illustrates the treatment of a mammal after spinal cord injury.

A mammal suffering from spinal cord injury is identified and administered an effective amount of a composition comprising an anti-CS-E antibody. The appropriate dosage and treatment regimen can be readily determined by the skilled artisan based on a number of factors including the nature of the anti-CS-E antibody, the route of administration and the mammal's injury state. Spinal cord injury treatment efficacy is evaluated by observing delay or slowing of injury progression, amelioration or palliation of the injury state.

Example 7

Treatment of Inflammatory Disease

This example illustrates the treatment of an inflammatory disease using an antibody to CS-E.

A mammal suffering from an inflammatory disease associated with TNFα is identified and administered an effective amount of a composition comprising an anti-CS-E antibody. The appropriate dosage and treatment regimen can be readily determined by the skilled artisan based on a number of factors including the nature of the anti-CS-E antibody, the route of administration and the mammal's injury state. Treatment efficacy is evaluated by observing reduction in the symptoms of the disease.

Hybridoma Deposit

A hybridoma producing the antibody discussed above 2D11-2A10 is being deposited with the American Type Culture Collection, PO Box 1549, Manassas, Va. 20108, under the Terms of the Budapest Treaty. The Accession Number for the clone is PTA-10049.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The invention illustratively described herein suitably can be practiced in the absence of any element or elements, limitation or limitations that is not specifically disclosed herein. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention disclosed. Thus, it should be understood that although the present invention has been specifically disclosed by preferred embodiments and optional features, modification and variation of the concepts herein disclosed can be resorted to by those skilled in the art, and that such modifications and variations are considered to be within the scope of this invention as defined by the disclosure.

All patents and publications are herein incorporated by reference in their entireties to the same extent as if each individual publication was specifically and individually indicated to be incorporated by reference.

What is claimed is:

1. A method of generating an antibody comprising:
   (a) synthesizing a population of chondroitin sulfates, wherein individual members of said population are oligosaccharides made of one subunit selected from the group consisting of:

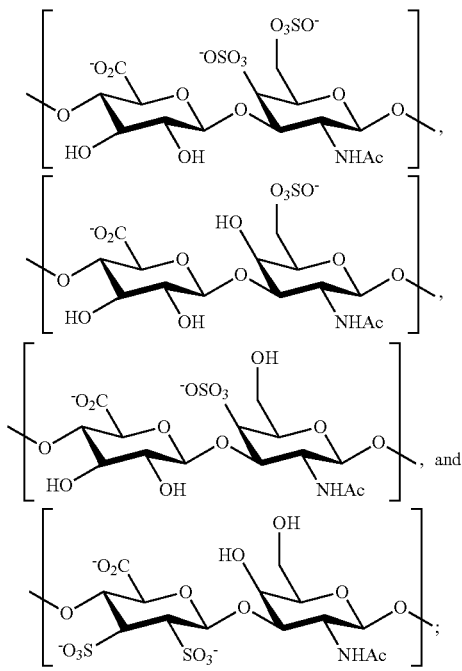

(b) inoculating a host animal with said population of chondroitin sulfates, wherein said inoculation induces in said host animal the production of one or more antibodies that selectively bind to said chondroitin sulfates; and
   (c) selecting from said one or more antibodies an antibody that selectively binds to an epitope recognized by antibody 2D11-2A10.

2. The method of claim 1, wherein said selecting comprises purifying said antibody from the serum of said host animal.

3. The method of claim 1, wherein said method further comprises isolating spleen cells of the inoculated host animal, fusing said spleen cells with a myeloma cell line to generate one or more hybridomas, and screening said hybridomas for antibodies which selectively bind to an epitope recognized by antibody 2D11-2A10.

4. The method of claim 1, wherein said method further comprises:
   (a) isolating genetic material from said host animal that encodes the antibody or a portion thereof;
   (b) introducing said genetic material into a suitable expression vector to produce an expression vector comprising said genetic material; and
   (c) transfecting said expression vector comprising said genetic material into host cells.

\* \* \* \* \*